United States Patent [19]

Granelli

[11] Patent Number: 5,736,003
[45] Date of Patent: Apr. 7, 1998

[54] APPARATUS FOR CONCENTRATING UREA SOLUTIONS UNDER VACUUM

[75] Inventor: Franco Granelli, Milan, Italy

[73] Assignee: Snamprogetti S.p.A., St. Donato, Italy

[21] Appl. No.: 513,251

[22] Filed: Aug. 10, 1995

Related U.S. Application Data

[60] Continuation of Ser. No. 118,146, Sep. 8, 1993, abandoned, which is a division of Ser. No. 687,116, Apr. 18, 1991, Pat. No. 5,273,623.

[30] Foreign Application Priority Data

Apr. 24, 1990 [IT] Italy ............................... 20129A

[51] Int. Cl.$^6$ ........................................ B01D 1/00
[52] U.S. Cl. ............... 159/31; 159/4.01; 159/DIG. 16; 202/152; 202/205; 202/234
[58] Field of Search ................ 159/47.2, 48.1, 159/16.3, 31, 46, 901, 4.4, 4.01, DIG. 16; 202/205, 234, 152; 203/91, DIG. 11; 564/73; 95/261

[56] References Cited

U.S. PATENT DOCUMENTS

| | | | |
|---|---|---|---|
| 2,702,949 | 3/1955 | Parker | 159/4.4 |
| 2,933,526 | 4/1960 | Guyer et al. | |
| 2,961,464 | 11/1960 | Kaasenbrood | |
| 3,130,225 | 4/1964 | Friend | |
| 3,146,263 | 8/1964 | Otsuka | 159/47.2 |
| 3,147,174 | 9/1964 | Cook | |
| 3,223,145 | 12/1965 | Templeton et al. | |
| 3,348,599 | 10/1967 | Lohstoeter et al. | 159/4.4 |
| 3,491,821 | 1/1970 | Graumann et al. | |
| 3,930,931 | 1/1976 | Baughman | 159/4.4 |
| 3,985,538 | 10/1976 | Hicks | |
| 4,069,253 | 1/1978 | Kanai et al. | |
| 4,219,589 | 8/1980 | Niks et al. | |
| 4,285,830 | 8/1981 | Miller | |
| 4,376,010 | 3/1983 | Gauvin | 159/16.3 |
| 4,539,077 | 9/1985 | Jonckers et al. | |
| 5,047,124 | 9/1991 | Haberland | 159/901 |
| 5,232,550 | 8/1993 | Takashi et al. | 159/DIG. 16 |

FOREIGN PATENT DOCUMENTS

| | | |
|---|---|---|
| 222354 | 12/1957 | Australia |
| 681148 | 3/1964 | Canada |
| 1490111 | 6/1989 | Russian Federation |
| 926781 | 6/1957 | United Kingdom |
| 2040711 | 1/1980 | United Kingdom |

*Primary Examiner*—Hien Tran
*Attorney, Agent, or Firm*—George P. Hoare, Jr.; Rogers & Wells

[57] ABSTRACT

Process for vacuum-concentrating urea solutions in which the final step of evaporation of the urea solution under vacuum is carried out within the injection of overheated water vapor in the overhead portion of the concentrator, in order to counteract the formation and deposition of high-melting, fouling compounds derived from urea.

6 Claims, 2 Drawing Sheets

APPARATUS FOR CONCENTRATING UREA SOLUTIONS UNDER VACUUM

This is a continuation of application Ser. No. 08/118,146, filed Sep. 8, 1993, now abandoned, which is a divisional of application Ser. No. 07/687,116, filed Apr. 18, 1991, now U.S. Pat. No. 5,273,623.

The present invention relates to the production of urea, and, in particular, to the final step of concentration of the urea solution product of such a process, in which urea solution is concentrated until a practically pure, molten urea product is obtained, which is suitable for obtaining a solid granular, i.e., the "prilled" urea product.

All of the industrial processes presently used for producing urea are based on the direct synthesis of urea from ammonia and carbon dioxide, according to the overall reaction:

$$2\ NH_3 + CO_2 = CO(NH_2)_2 + H_2O$$

leading to the formation of an aqueous solution of urea at a concentration of about 75% by weight.

In reality, the process is much more complex, in that it is constituted by a plurality of equilibrium reaction following each other, which require separations and recycles in order to achieve yields very close to the total conversion of the reactants according to the above cited overall reaction.

The solution obtained from the industrial facilities still contains small amounts of ammonia and of carbon dioxide which have not been converted into urea, and which have not been removed and recycled through the intermediate steps of the process.

In its several uses, urea is essentially required as a solid product, consisting of substantially spherical granules of variable size, depending upon the use for which the product is destined. The granules are obtained by "prilling" or granulation (pellets).

The prilling or granulation treatments have to be fed with molten urea at a concentration of 99.5–99.8% by weight in the case of prilling treatments, and at a concentration which may be lower in the case of granulation treatments.

According to the conventional processes, the final concentration step is carried out inside vacuum evaporators in which the solution at about 75% by weight of urea is concentrated until molten urea at 99.5–99.8% is obtained.

In the most recent processes, the requirements of energy saving have caused the final concentration step to be subdivided into two sequential steps carried out under decreasing pressure. The first step is carried out under subatmospheric pressure (such as at a pressure of 0.25–0.5 abs.bar) up to concentrations of solutions of the product which are higher than 90% by weight of urea, such as up to concentrations of 92–96% by weight of urea, without there being a substantial energy consumption from vacuum production. The second step, which increases the concentration of solutions of the product up to 99.5–99.8% of urea, is carried out under high vacuum, with substantial energy being consumed only in order to remove the last portion of evaporated water from the concentrated solutions.

The concentration steps have to be carried at temperatures even higher than the solidification temperature of urea, in particular when the water content of the urea is so low as to no longer be able to provide any substantial solubilizing effect.

During the operation of final concentration, and in particular in the final concentration step of the two step concentration processes, a phenomenon of fouling of the upper portion of the concentrator (i.e., the vacuum evaporator), caused by the separated gas phase, takes place.

This fouling leads to incrustations which tend to accumulate over time, and requires such incrustations to be periodically removed, such as by programmed servicing, in order not to compromise the quality of the product or the efficiency of the facility. This programmed servicing prevents accidental stops of the process due to the falling down of the poorly soluble fouling incrustations—which might cause duct cloggings and difficulties in product discharge.

The phenomenon of the formation of such incrustations is very complex and proceeds according to rather unknown reactions and kinetics. It is generally attributed to the fact that during the final concentration step, in the gas phase which develops inside the concentrator (i.e., the vacuum evaporator), there are, in addition to the water vapor, residual amounts of ammonia, carbon dioxide and still other volatile components arising from the urea decomposition. These components are contained together with entrained suspended particles of molten urea, the amount which is small, but not negligible over time.

The formation of the incrustations in the upper portion of the concentrator (i.e., the vacuum evaporator), caused by the gas phase which is developed during the final concentration step, is attributed to these components contained in said gas phase. In fact, the incrustations formed, besides urea and biuret (which are soluble in water), also contain longer-chain compounds (which are insoluble in water), such as triuret and its higher homologous products, which are formed by urea condensation. The incrustations contain, as well, other compounds such as cyanuric acid.

Those reactions forming the incrustations are thought to take place on urea particles deposited on the top walls of the concentrator (i.e., the vacuum evaporator), and are thought to be favored by low pressure and relatively high temperature.

The reactions leading to the formation of such incrustations are quantitatively negligible with respect to the process yields, in that the reactions causing the formation of incrustations proceed very slowly, but in the long term the reactions are the cause of the incrustations which are deposited on the walls of the upper portion of the concentrator. The resulting incrustations are difficult to remove and to be disposed of, in that they are practically useless.

The above-mentioned compounds display higher melting points than urea (132° C.): biuret melts at 190° C. and triuret melts at 231° C. Their solubility in water is very low, and in order to remove the incrustations only mechanical cleaning remains, which should be carried out during stops of the facility.

The process according to the present invention consists of a process for concentrating under vacuum urea solutions which already are at a high concentration of urea, until molten urea at a concentration of 99.5–99.8% by weight of urea is obtained, without any substantial formation of insoluble incrustations taking place in the concentrator. According to the present invention, the process is characterized by carrying out the final vacuum concentration step by injecting inside the upper portion of the concentrator, in which the development of the gas phase leading to the incrustations takes place, water vapor which expands and overheats, with the composition and the weight ratio between the gas phase and produced molten urea being thus varied.

The injection of overheated water vapor can be carried out either continuously or intermittently, with the amount of water vapor being fed comprised within the range of from 10% to 100% by weight, and preferably comprised within the range of from 20% to 50% by weight, relative to the weight of the gas phase evolved during the final concentration step.

DETAILED DESCRIPTION OF THE DRAWINGS

In order to illustrate the characteristics and advantages of the present invention, the process and apparatus are disclosed in the following by referring to a typical form of a practical embodiment thereof, reported in the hereto attached figures for merely illustrative, non-limitative purposes.

Figure 1:
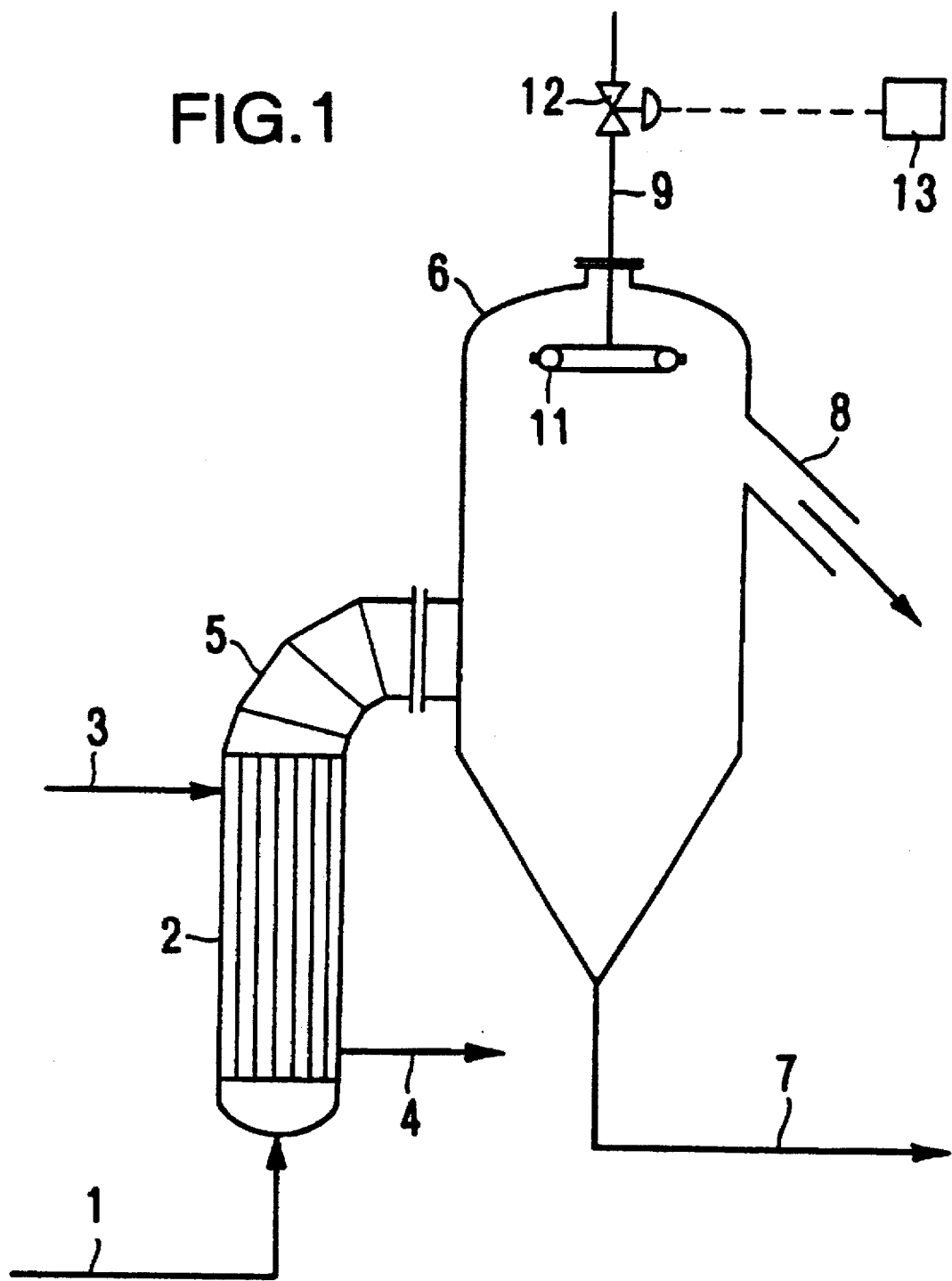
FIG. 1 is a diagrammatical illustration of a typical apparatus for operating the process of the present invention.
Figure 2A:
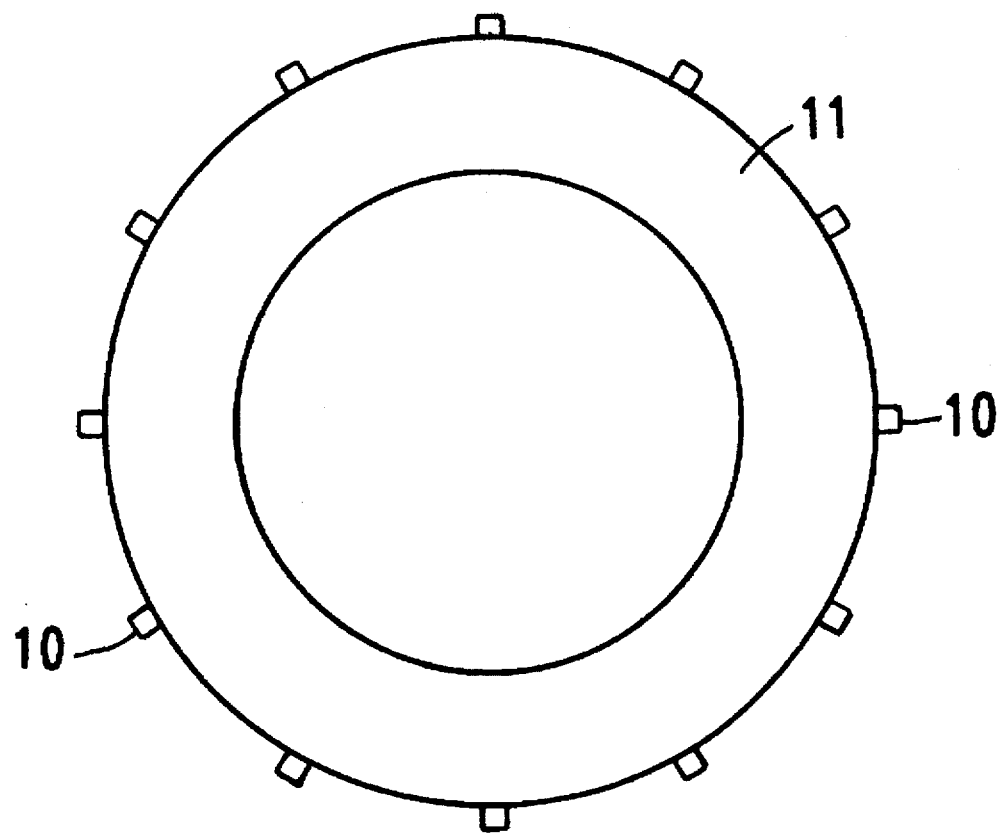
FIG. 2 is a detailed view of the toroidal distributor contained in the separator.
Figure 2B:
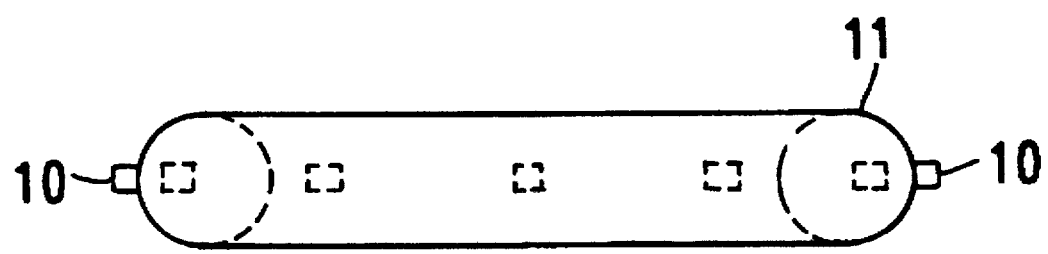

Referring to the drawing, FIGS. 1 and 2 show a tube-bundle type heat exchange (2) with a feed pipe (1) for the urea solution, a steam feed pipe (3), a condensate discharge pipe (4), and a gas-liquid phase discharge pipe (5). The discharge pipe (5) leads to a cylindrical separator (6) which has at the bottom a discharge pipe (7) for molten urea and at the upper portion a discharge pipe (8) for drawings off the gas phase. A pipe (9) for injecting overheated water vapor which extends through the top and into the upper portion of the separator (6) and is attached to a toroidal distributor (11) with nozzles (10) installed so that the water vapor can be injected both axially and radially. A valve (12) controls, with the aid of a timer (13), the supply of water vapor.

The urea solution, already concentrated in the atmospheric concentration step up to a purity of 92–96% by weight of urea, is fed by the pipe 1 to the heat exchanger 2 of tube-bundle type, wherein it is heated to a temperature substantially higher than the solidification temperature of urea, i.e., of 134°–144° C. on the average.

The pressure inside the heat exchanger 2, is kept comprised within the range of from 0.02 to 0.1 abs.bar, by the effect of vacuum generators, typically multi-step steam ejectors, connected with the subsequent separator vessel.

Inside the tube-bundle type heat exchanger 2, two phases are formed: a liquid phase, substantially constituted by molten urea at 99.5–99.8% by weight of urea, and a dispersed gas phase, constituted by water vapor and a small portion of ammonia, carbon dioxide and still other volatile compounds derived from urea decomposition. The necessary heat is supplied to the heat exchanger as steam fed to the jacket side of the heat exchanger through the pipe 3, and discharged as condensate through the pipe 4.

The mixed gas-liquid phase generated inside the tube bundle of the heat exchanger 2 is fed through the pipe 5 to the separator 6 of cylindrical shape, in which the separation of the two phases takes place. According to a preferred form of practical embodiment of the present invention, the gas-liquid phase is fed tangentially to the internal cylindrical surface of the separator, such as to take advantage of the centrifugal effect caused by the difference in density of the two phases and to cause the separation of the gas phase to develop in a centripetal direction—typical of a cyclone separator. A relative speed between the two phases is obtained which is much smaller than one might expect to obtain by computing it on the basis of the surface-area of the cross-section of the separator, with the effect of purely dynamic entraining of suspended urea particles—which result in being a determining factor of fouling—being hence reduced. The bottom portion of the separator 6 is made with an acute-angle conical bottom, such as to limit the residence time of the molten urea, and such as to limit the entraining of suspended urea particles in an upwardly direction. From the bottom of the separator 6, molten urea is sent by means of the pipe 7 to the step of solidification in particulate form, i.e., "prilling" or granulation.

On the other hand, the separated gas phase is laterally drawn from the upper portion of the separator 6 by means of the pipe 8 and is sent to a conventional vacuum-condensation unit now shown in the figure. Typically, the vacuum-condensation unit can be constituted by a plurality of vapor ejectors installed in cascade with the relevant condensers.

The portion of the separator 6 which is affected by fouling is, in general, the top spherical ceiling of the separator and its adjacent cylindrical walls. According to the present invention, overheated water vapor is injected into the upper portion of the separator 6 by means of the pipe 9 and is distributed by means of a plurality of nozzles which direct their jets toward the walls of the upper spherical ceiling and the cylindrical walls adjacent to it. According to a typical form of practical embodiment of the present invention, the nozzles 10, as illustrated in FIG. 2, are installed on a toroidal distributor 11, so as to inject the water vapor both axially and radially, with a region being established which is protected by the water vapor from the above said fouling.

The number of the nozzles can be comprised within the range of from 6 to 24, and preferably of from 8 to 16, and can also be subdivided on a plurality of distributors.

The supply of water vapor through the pipe 9 is controlled by the valve 12, and the supply of water vapor can take place continuously or intermittently with the aid of a timer 13. In fact, the present applicant has found that the action of protection against fouling is effective even if water vapor is only intermittently injected into the separator 6.

In principle, the intermittent injection is easier to be applied in situation where already existing facilities have to be modified, because the available capacity of the already existing vacuum condensation units and vacuum generators has to be taken into due account. In new facilities the continuous injection—which does not generate oscillations in the performance of vacuum generation units and of the condensers installed downstream the separator 6—is more easily applied.

EXAMPLE

In an already existing facility for urea production of rated production capacity of 1000 tons daily, the flow rate of urea solution fed to final concentration is of:

| Urea | 41,717 kg/h |
|---|---|
| Ammonia | 9 kg/h |
| Carbon dioxide | 4 kg/h |
| Water | 2,650 kg/h |

The final concentration step is carried out at the temperature of 138° C. and under a pressure of 0.03 abs.bar, and yields a molten mass of urea containing 41,620 kg/h of urea and 104 kg/h of water. A gas phase also developed, which contains:

| Decomposed and entrained urea | 97 kg/h |
|---|---|
| Ammonia | 9 kg/h |
| Carbon dioxide | 4 kg/h |
| Water | 2,546 kg/h |

In this concentration section, a considerable fouling took place in the upper portion of the separator. The fouling incrustations were removed by water washing every three weeks and mechanical cleaning every year.

The facility was modified in order to inject water vapor means of a toroidal distributor equipped with 8 nozzles to the upper portion of the separator 6, as shown in the hereto attached figure.

During an approximately 1-year long production time (i.e., during the time interval between two annual servicing operations), water vapor at 150° C. was fed at a flow rate of 450 kg/h. The water vapor feed took place intermittently, i.e., a feed every two hours and each feed having a duration of about 10 minutes, with the aid of the timer 13.

After a 1-year run, at the subsequent servicing stop, the fouling was shown to have been reduced by about 90% as compared to the preceding runs carried out with no water vapor injection.

I claim:

1. An apparatus for concentrating a urea solution under a vacuum so as to result in molten urea being obtained by separation thereof from a gas phase, said apparatus comprising a heat exchanger, a separator operably affixed to said heat exchanger via means for introducing a urea solution into said separator, means for laterally removing vapor from said separator, and means for injecting superheated water vapor into said separator so as to protect a region within said separator from the formation of insoluble incrustations, wherein the position of said means for injecting superheated water vapor into said separator is above said means for laterally removing vapor from the separator, the position of said means for laterally removing vapor from said separator in turn is above said means for introducing the urea solution into said separator.

2. The apparatus according to claim 1, wherein said means for injecting the superheated water vapor comprises a distributor having at least one nozzle.

3. The apparatus according to claim 2, wherein the distributor is toroidal.

4. The apparatus according to claim 3, wherein said toroidal distributor has from 6 to 24 nozzles associated therewith.

5. The apparatus according to claim 4, wherein said toroidal distributor has from 8 to 16 nozzles associated therewith.

6. The apparatus according to claim 1, wherein the means for injecting the superheated water vapor comprises a plurality of distributors each having a plurality of nozzles.

* * * * *